United States Patent [19]
Pinvidic et al.

[11] Patent Number: 6,157,455
[45] Date of Patent: Dec. 5, 2000

[54] METHOD AND APPARATUS FOR DETERMINING THE CALORIFIC VALUE OF A NATURAL GAS OPTICALLY AND IN REAL TIME

[75] Inventors: Jean-Jacques Pinvidic, Charenton-le-Pont; Laurence Juen-Grenier, Saint-Savourin; Gérard Pelous, Aix-en-Provence, all of France

[73] Assignee: Gaz de France, France

[21] Appl. No.: 09/092,434

[22] Filed: Jun. 5, 1998

[30] Foreign Application Priority Data

Jun. 6, 1997 [FR] France ................................ 97 07024

[51] Int. Cl.$^7$ .................................................. G01N 21/25
[52] U.S. Cl. ............................................ 356/437; 250/343
[58] Field of Search ................................ 356/437; 250/343

[56] References Cited

U.S. PATENT DOCUMENTS

| | | | |
|---|---|---|---|
| 3,950,101 | 4/1976 | Dewey, Jr. . | |
| 4,553,032 | 11/1985 | Lo et al. . | |
| 4,567,366 | 1/1986 | Shinohar | 250/343 |
| 4,594,510 | 6/1986 | Brown et al. | 250/343 |
| 4,914,719 | 4/1990 | Conlon et al. | 250/343 |
| 4,996,431 | 2/1991 | Bonne et al. | 250/343 |
| 5,349,189 | 9/1994 | Maggard | 250/343 |
| 5,822,058 | 10/1998 | Adler-Golden et al. | 356/303 |

FOREIGN PATENT DOCUMENTS

| | | |
|---|---|---|
| 2735236 | 9/1995 | France . |
| 9606344 | 2/1996 | WIPO . |

*Primary Examiner*—Richard A. Rosenberger
*Attorney, Agent, or Firm*—Ostrolenk, Faber, Gerb & Soffen, LLP

[57] ABSTRACT

Natural gas whose calorific value is to be determined is illuminated with a light beam that is applied by a measurement head and that defines three measurement bands with different wavelength ranges each having a bandwidth of 10 nm to 20 nm and all situated in the near infrared. The intensity of each light beam is measured after it has passed through the gas, and the calorific value of the natural gas is computed in situ and in real time on the basis of the optical absorption values obtained by measuring the intensities of the light beam after it has passed through the gas.

19 Claims, 3 Drawing Sheets

METHOD AND APPARATUS FOR DETERMINING THE CALORIFIC VALUE OF A NATURAL GAS OPTICALLY AND IN REAL TIME

FIELD OF THE INVENTION

The present invention relates to a method of determining the calorific value of a natural gas optically and in real time by measuring the absorption of a light beam by the components of the gas, in which the gas is illuminated by a light beam of predetermined characteristics, the intensity of the light beam is measured after it has passed through the gas, and the calorific value of the natural gas is calculated from the optical absorption obtained on the basis of the measured intensity of the light beam after it has passed through the gas.

The invention also relates to apparatus for implementing the method.

BACKGROUND OF THE INVENTION

It is desirable to be able to perform energy metering at the point of delivery of natural gas, at least for certain users, such as industry, or for certain groups of users within a public distribution network.

Energy metering at the point of delivery is defined as measuring, in a single location, magnitudes that enable the quantity of energy delivered to be determined. These magnitudes are, in particular, volume, pressure, temperature, gas composition, calorific value (CV), energy flow rate.

The point of delivery corresponds to the expansion station where the gas is expanded, regulated, and metered. Such a station is designed to guarantee continuity of gas supply even in the event of one of the elements of the station failing.

The composition of natural gas as supplied to transport and distribution networks can vary, which gives rise to variations in the calorific value of the gas, and consequently to variations in the mount of energy supplied for given volume of delivered gas.

Industrial clients of transport and distribution networks desire to be able to optimize methods that require the use of gas, and consequently, even if they do not know the exact composition of the natural gas used, they would still like to be able to determine the calorific value of the natural gas they are consuming.

For their part, the suppliers of gas would like to know the calorific value of the gas they have delivered so as to be able to bill their clients as a function of the mount of energy actually supplied instead of merely as a function of the volume of gas delivered, since volume corresponds to varying mounts of energy depending on the calorific value of the gas.

For all of these reasons, it is desirable to be able to determine the calorific value (specifically the calorific value or CV) of a natural gas with accuracy to within better than 1%, and if possible to within about 0.5%, by means of a method that is of reasonable cost and that is easy to implement.

Proposals have already been made to measure CV using fast chromatographs or calorimeters. Those methods remain relatively expensive and they are not fully satisfactory for the intended application since they require samples of the gas to be taken, measurements to be performed in special test cabins, and standard gas to be used, all of which implies that the length of time required to perform a measurement prevents it from being done in real time.

Proposals have also been made, in particular in document FR-A-2 735 236, to use an infrared technique to measure the calorific value of a natural gas. In that technique, a specific absorption line in the near infrared is initially selected for each component of the gas, the gas is illuminated by a laser beam having a wavelength close to the wavelength of the selected absorption lines, and a spectrum width that is narrower than the widths of the selected absorption lines, the wavelength of the light beam is varied to scan through the selected absorption lines, the intensity of the light beam after passing through the gas is measured both at the wavelengths of the selected absorption lines and at other wavelengths, and the relative concentrations of the components of the gas are deduced therefrom by calculation and hence the calorific value of the gas can also be deduced.

Such a method requires the use of a system having a tunable laser diode or the equivalent, which is expensive, it makes use of high resolution spectroscopic techniques which remain complex to implement, it requires good prior knowledge about the nature and the composition of the gas in order subsequently to be able to determine its calorific value with sufficient accuracy, and it cannot be applied appropriately to natural gases whose components do not present a structure with well-isolated absorption lines, or that present absorption lines that overlap completely or in part.

OBJECTS AND SUMMARY OF THE INVENTION

The present invention seeks to remedy the above-mentioned drawbacks and to enable the calorific value of a natural gas to be measured accurately, in real time, on site, conveniently, and at low cost, regardless of the composition of the gas over a wide range of possible compositions, and without it being necessary to use specialized personnel or equipment other than equipment which is used in standard manner in telecommunications.

These objects are achieved by a method of determining the calorific value of a natural gas optically and in real time by measuring the absorption of a light beam by the components of the gas, in which the gas is illuminated by a light beam of predetermined characteristics, the intensity of the light beam is measured after it has passed through the gas, and the calorific value of the natural gas is calculated from the optical absorption obtained on the basis of the measured intensity of the light beam after it has passed through the gas, wherein the gas is illuminated by means of a light beam defining three measurement bands defining different wavelength ranges, each having a bandwidth of 10 nm to 20 nm and situated in the near infrared, the measurement bands define wavelength ranges situated outside the absorption ranges of non-hydrocarbon components, and a reference band is also used defining a range of wavelengths having a bandwidth of 10 nm to 20 nm and situated in the near infrared outside the wavelength ranges of the measurement bands and of the absorption ranges of the gas.

Preferably, the measurement bands are situated in three zones defined by the following wavelength ranges 1.111 $\mu$m to 1.190 $\mu$m, 1.1315 $\mu$m to 1.429 $\mu$m, and 1.613 $\mu$m to 1.818 $\mu$m, in which the hydrocarbons constituting natural gas present significant absorption.

By way of example, three measurement bands are defined lying in the following wavelength ranges: 1.176 $\mu$m to 1.190 $\mu$m; 1.315 $\mu$m to 1.325 $\mu$m; and 1.62 $\mu$m to 1.64 $\mu$m.

The reference band may itself define a wavelength range of 1.24 $\mu$m to 1.25 $\mu$m.

Advantageously, the transmission coefficient $T_i$ of the natural gas in a measurement band i is determined by the ratio between the light intensity $I_i$ measured in the measurement band concerned and the light intensity $I_r$ measured in the reference band.

To improve the accuracy of the result, it is possible to calculate the calorific value of the natural gas from a collection of N individual measurements of the intensity of the light beam that has passed through the gas, where N is greater than 5, and close to 10 for example.

The light beam defines three measurement bands, and the calorific value (Cv) of the natural gas is deduced from the measured transmission coefficients $T_1$, $T_2$, and $T_3$ of the natural gas in the three measurement bands using the following relationship:

$$CV = \alpha + \beta_1 ln(T_1) + \delta_2 ln(T_2) + \gamma_3 ln(T_3)$$

where $\alpha$, $\beta_1$, $\delta_2$, and $\gamma_3$ represent coefficients determined from calibration tests.

In an aspect of the method, the pressure and the temperature of the gas are also measured, and when determining the calorific value of the natural gas by computation, the measured pressure p and temperature $\theta$ of the gas are taken into account.

The light beam defines three measurement bands, and the calorific value (CV) of the natural gas is deduced from the measured transmission coefficients $T_1$, $T_2$, and $T_3$ of the natural gas in the three measurement bands using the following relationship:

$$CV = [\alpha(\theta/p) + \alpha_2] + [\beta_{11}(\theta/p) + \beta_{12}]ln(T_1) + [\delta_{21}(\theta/p) + \delta_{22}]ln(T_2) + [\gamma_{31}(\theta/p) + \gamma_{32}]ln(T_3)$$

where $\alpha$, $\alpha_2$, $\beta_{11}$, $\beta_{12}$, $\delta_{21}$, $\delta_{22}$, $\gamma_{31}$, and $\gamma_{32}$ are coefficients determined from calibration tests.

The invention also provides apparatus for determining the calorific value of a natural gas optically and in real time by implementing the above-defined method, the apparatus comprising an emitter unit fitted with a light source to cause a light beam to travel in a gas duct, a receiver unit fitted with a photodetector to receive the light beam after it has passed through the gas and to generate signals corresponding to absorption by the gas of the light beam emitted by the source, and an electronic control module for computing the calorific value of the natural gas from the signals emitted by the photodetector, wherein the emitter unit comprises a light source emitting in the near infrared and means for defining three measurement bands constituted by different wavelength ranges each having a bandwidth of 10 nm to 20 nm, wherein the receiver unit comprises a photodetector constituted by a photodiode and an analog-to-digital converter, and wherein the electronic control module has at least one microprocessor.

The apparatus comprises a measuring head comprising a first optical fiber linking it with the emitter unit, a second optical fiber linking it with the receiver unit, a housing into which the first and second optical fibers penetrate and which includes a porthole-forming wall which constitutes a portion of the wall of the gas duct to enable optical collimator components disposed in the housing to emit an incident light beam from the first optical fiber into the inside of the gas duct and to receive from the gas duct a reflected light beam, and a filtering porous envelope disposed inside the gas duct, partially defined by said porthole-forming wall, and containing a retroreflector to receive said incident light beam and to create said reflected light beam.

Advantageously, the measuring head is disposed in a gas duct which constitutes a bypass duct in parallel with a main pipe and connected thereto via isolating valves.

In a particular embodiment, for each measurement band, the light source comprises an emitter module comprising a light emitting diode emitting a narrow band of wavelengths, having a bandwidth of a few tens of nanometers, the emission of each light emitting diode being modulated at a respective frequency, a first lens which spreads the beam from the corresponding light emitting diode over an interference filter, and a second lens which focuses the beam from the corresponding interference filter onto an optical fiber, with each optical fiber being connected to an optical coupling device.

Advantageously, the total emission of light from the optical coupling device is shared mainly over a measurement channel serving to emit a light beam to the gas duct and subsidiarily over a monitoring channel for verifying proper operation of the light source.

The receiver unit comprises a lens for focusing on the photodiode of the photodetector, an AC amplifier for transforming the current information delivered by the photodiode into voltage information, a demodulator which filters the signal at the various modulation frequencies of the emitter modules, and said analog-to-digital converter.

In another particular embodiment, the light source comprises a single broadband source such as a tungsten-halogen lamp associated with a reflector and with a first lens, a wheel of interference filters defining the measurement bands and enabling wavelengths characteristic of the various measurement bands to be selected in succession, and a lens for focusing onto an optical fiber.

The receiver unit comprises a lens for focusing on the photodiode of the photodetector, a DC amplifier, and said analog-to-digital converter.

The electronic control module comprises means for synchronizing the various measurement channels corresponding to the various measurement bands, and means for testing proper operation of the apparatus.

BRIEF DESCRIPTION OF THE DRAWINGS

Other characteristics and advantages of the invention appear from the following description of particular embodiments of the invention given with reference to the accompanying drawings, in which.

MORE DETAILED DESCRIPTION

Figure 1:
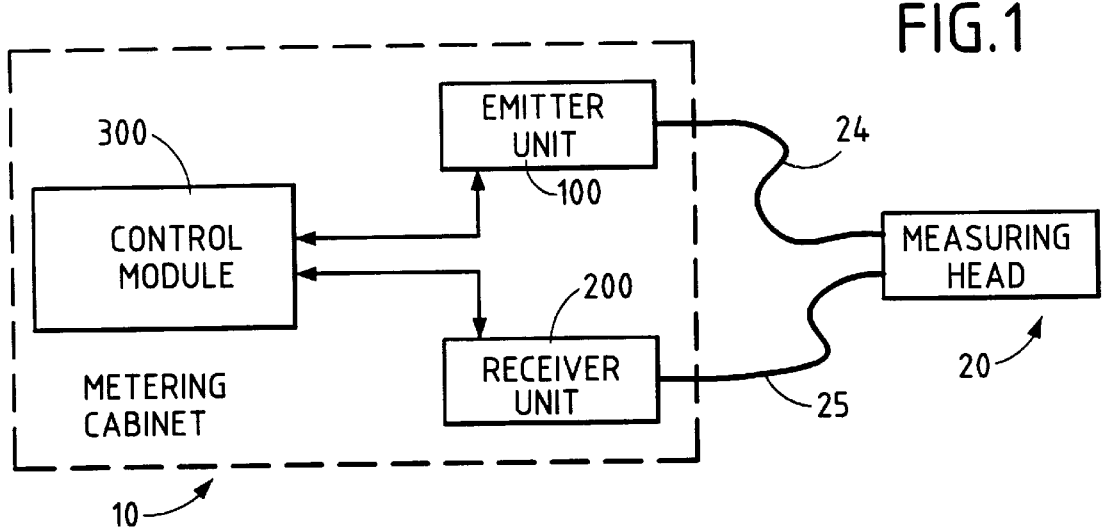
FIG. 1 is a block diagram showing the overall architecture of gas metering apparatus implementing the invention.

The overall architecture of apparatus implementing the method of the invention is shown in FIG. 1.

A measuring head 20 is placed directly on the natural gas feed pipe or on a branch duct. The measuring head 20 is connected to a metering cabinet 10 by optical fibers 24 and 25. The optical fibers 24 and 25 may be about 200 meters (m) long, such that only optical components that convey low powers, less than 5 mW, come into contact with the gas, and so that the electrical components are placed in a zone where there is no risk of deflagration.

By way of example, the optical fibers 24 and 25 may be HCL silica/silica multimode fibers from SPECTRAN, having a core diameter of 550 μm and an outside diameter of 750 μm. The attenuation of such optical fibers is less than 10 dB/km, i.e. less tan 40% for 200 meters. Naturally, for shorter link distances, of the order of a few tens of meters, it is also possible to use polymer optical fibers which are cheaper.

The metering cabinet 10 essentially comprises an emitter unit 100 which generates a light signal that is applied to the optical fiber 24 so as subsequently to pass through the gas that is to be analyzed in the measurement head 20 where a portion of the light signal is absorbed. The portion of the light signal that is not absorbed by the gas travels along the optical fiber 25 to be applied to a receiver unit 200 where the light signal is picked up and transformed into an analog signal, and then converted into a digital signal. Measurements are processed and the various operations are synchronized within an electronic control module 300 which is functionally connected to the emitter unit 100 and to the receiver unit 200.

The measuring head 20 may be placed transversely relative to the duct in which the gas flows. The measuring head 20 may also, advantageously, be implanted on a bypass duct 2 which is placed in parallel with the main pipe 1 (FIG. 2), thereby making it possible to perform maintenance operations without interfering with gas delivery. The bypass duct 2 opens out into the main pipe 1 via two lengths of duct 3 and 4 having respective isolating valves 5 and 6.

Figure 2:
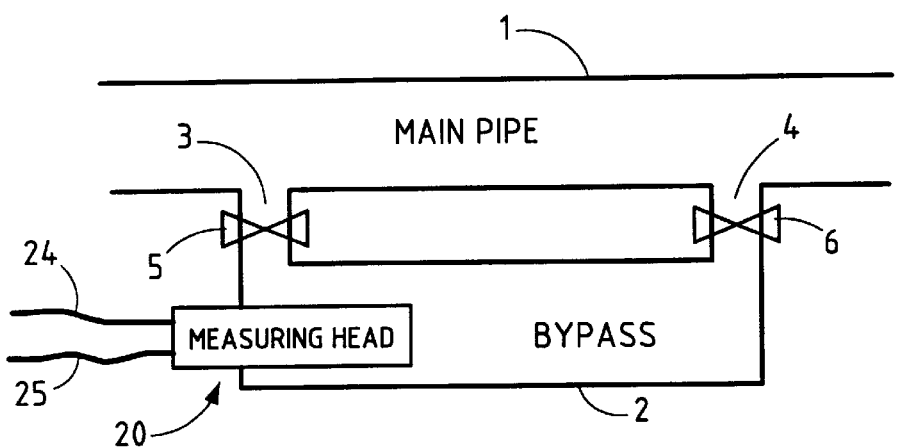
FIG. 2 is a diagram showing how a measurement head of gas metering apparatus of the invention is installed relative to a gas-conveying pipe.

In the embodiment of FIG. 2, the measuring head 20 is situated where the inlet length of duct 3 opens out and the axis of the measuring head and of the light path (e.g. having a length of 0.3 m) lies on the axis of the bypass duct 2 where it extends parallel to the main pipe 1. Such a configuration makes it possible to standardize the equipment since under such circumstances there is no need to match the mechanical interfaces and the length of the light path to a multitude of pipe diameters.

Figure 3:
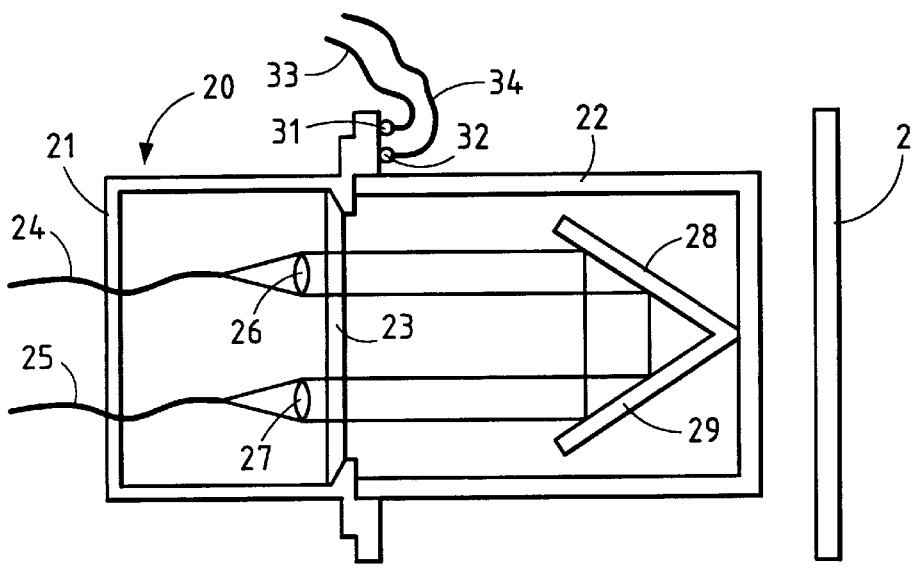
FIG. 3 is a diagram showing in greater detail one particular embodiment of a measurement head for metering apparatus of the invention.

FIG. 3 shows an example of a measuring head 20 for performing a measurement in a duct 2 either on the axis of the duct as mentioned above, or else transversely. The measuring head 20 comprises a housing 21 into which the optical fibers 24 and 25 penetrate, said housing 21 having a porthole-forming wall 23 which constitutes a wall portion of the gas duct 2 and which enables optical collimator components 26 and 27 located inside the housing 21 to emit an incident light beam coming from the first optical fiber 24 into the inside of the gas duct, and to receive in return a reflected light beam. The light beam coming from the optical fiber 24 is thus transformed into a parallel beam by the lens 26 to pass through the gas mixture, thereby providing the advantage of increasing the volume sampled and of minimizing the risk of incidents on the path through the gas. The light beam coming from the lens 26 is reflected by a retroreflector made up of three mirrors 28, 29 constituting a corner of a cube which is a reflecting tri-rectangular trihedron. The retroreflector returns a parallel beam towards the lens 27 which refocuses the light beam onto the return optical fiber 25. A filtering porous envelope 22 extends the housing 21 inside the duct 22 and provides mechanical support for the mirrors 28, 29. This envelope 22 is made of a material that is permeable to gas but proof against dust so as to limit the mount of impurity that is deposited on the faces of the corner of a cube placed inside the envelope 22, and also to limit deposits on the porthole 23. Temperature and pressure sensors 31 and 32 may be placed in the duct 2 in the vicinity of the measurement head 20 and connected to the metering cabinet 10 by link cables 33 and 34.

Before describing various embodiments of the functional components of the metering cabinet 10, with reference to FIGS. 4 to 8, the essential characteristics of the method of the invention for determining the calorific value (CV) of natural gas are described below.

According to the invention, the optical absorption of the natural gas flowing in the duct is measured in various wavelength bands situated in the near infrared, with each having a bandwidth of 10 nm to 20 nm. Measurement is thus performed in relative manner, since it relies on establishing a direct link between CV and infrared absorption, without prior determination of the concentration of each of the components of the gas.

By way of preferred example, the following three measurement wavelengths bands are used:

band 1: 1.176 μm to 1.190 μm (with a mean transmission coefficient $T_1$=85% for a light path length of 0.3 m);

band 2: 1.315 μm to 1.325 μm (with a mean transmission coefficient $T_2$=90% for a light path length of 0.3 m); and band 3: 1.62 μm to 1.64 μm (with a mean transmission coefficient $T_3$=75% for a light path length of 0.3 m)

These three measurement bands correspond to wavelength ranges situated outside the absorption ranges of non-hydrocarbon components of the gas. Bands 2 and 3 are mainly sensitive to methane while band 1 is mainly sensitive to other alkanes.

More generally, the various measurement bands of 10 nm to 20 nm bandwidth situated in the near infrared are advantageously selected to lie within the following three zones in which the hydrocarbons making up natural gas present significant mounts of absorption:

1.111 μm to 1.190 μm 1.333 μm to 1.429 μm 1.613 μm to 1.818 μm

By working in the near infrared, it is possible to use light sources and photodetectors that are not cooled, unlike longer wavelengths where implementation becomes more complex.

CV can be deduced from optical absorption because, in particular for wavelengths in the above-defined ranges, both CV and light absorption are tied to molecular structure, and in particular to the number of C—H bonds contained in a molecule.

It is important to use relatively broad wavelength bands (10 nm to 20 nm) to measure absorption of a light beam by natural gas containing a mixture of alkanes, since there is no available structure of well-isolated absorption lines, except for methane, and since the absorption bands of the various components of the gas are superposed almost completely.

If three wavelength bands are used for measurement, such as the bands 1 to 3, then the CV of the analyzed natural gas can be deduced from the measured transmission coefficients $T_1$, $T_2$, and $T_3$ of the natural gas in the three measurement bands by using the following relationship:

$$CV = \alpha + \beta_1 ln(T_1) + \delta_2 ln(T_2) + \gamma_3 ln(T_3)$$

where $\alpha$, $\beta_1$, $\beta_2$, and $\gamma_3$ represent coefficients determined on the basis of calibration tests, so as to minimize the differences between the CVs calculated on the basis of theory or measured using calibrated means for a set of gas mixture samples of various known compositions covering a wide range of hydrocarbon concentrations, and the CVs deduced from the transmission coefficients $T_1$, $T_2$, and $T_3$ measured in the various measurement bands using said gas mixture samples.

For the gas mixture samples used, composition can be defined in terms of molar concentrations corrected for phenomena associated with non-ideal mixing. First, it is possible to define a corrected molar concentration $X_i$ which is equal to the ratio between the molar fraction of the component i and the coefficient of compressibility Z of the gas mixture under consideration. This makes it possible to avoid determining the coefficient of compressibility of the mixture under study.

When studying samples of hydrocarbon gas mixtures, representing various types of natural gas and contributing to determining coefficients enabling CV to be calculated from the mean transmission coefficients $T_1$, $T_2$, and $T_3$ in each measurement band, the transmission coefficient of a mixture $T\lambda$ for a given wavelength is modelled on the basis of the following formula:

$$T\lambda = \exp\left(-(\Sigma_i X_i \alpha_{i\lambda}) \cdot (P_t) / (Z\theta)\right)$$

where:

$X_i$: molar fraction of component i $\alpha_{i\lambda}$: absorption coefficient of component i at wavelength $\lambda$ $P_t$: total pressure l: length of light path Z: coefficient of compressibility of the mixture $\theta$: temperature (K).

The transmission spectra of each of the mixtures studied are calculated spectrally using this principle. Then they are integrated over the three previously defined wavelength bands so as to determine mean transmission coefficients ($T_1$, $T_2$, and $T_3$) over each band.

The theoretical CVs expressed in kcal per mole of mixture are deduced from the equation:

$$CV_{mol} = \Sigma_i (X_i Cv_{moli})$$

where:

$X_i$: molar fraction of component i $CV_{moli}$: $CV_{mol}$ of component i.

The molar volume of the mixture is written:

$$V_{mol} = (ZR\theta)/(P_t)$$

where R is the perfect gas constant and Z, $\theta$ and $P_t$ have the same meanings as above, so it is possible to define a characteristic CV per unit volume of the mixture as follows:

$$CV_{vol} = (\Sigma_i(X_i CV_i)) \cdot ((P_t)/(ZR\theta))$$

It will be observed that molar CV, unlike volume CV is independent of temperature and pressure conditions.

Nevertheless, for the purpose of metering energy, in association with measuring a volume flow rate, it is volume CV that is of interest, and consequently it is volume CV that is used as the reference herein.

The outside temperatures at which natural gas is delivered may be evaluated as lying in the range −20° C. to +30° C.

Usual delivery pressures are 4 bars, but in some cases they may be as high as 10 bars or 16 bars.

For a delivery pressure of 4 bars, the extreme pressure values may be 3.5 bars and 4.5 bars.

A light path length of 0.3 m is well adapted to a mean delivery pressure of 4 bars.

For pressures of 10 bars and 16 bars, the light path length should be reduced to 12 cm and 7.5 cm, respectively.

When determining CV from mean optical transmission values $T_1$, $T_2$, and $T_3$ in the various measurement bands, accuracy can be improved if the coefficients determined for minimizing the differences between the CVs obtained theoretically and those obtained by measuring light absorption take into account the temperature $\theta$ of the gas and the pressure P of the gas in the vicinity of the measuring head.

Under such circumstances, the method of the invention makes it possible to determine CV from the following formula:

$$CV = [\alpha(\theta/P) + \alpha_2] + [\beta_{11}(\theta/P) + \beta_{12}]ln(T_1) + [\delta_{21}(\theta/P) + \delta_{22}]ln(T_2) + [\gamma_{31}(\theta/P) + \gamma_{32}]ln(T_3)$$

If the calibration tests take a significant number of gas mixtures of similar but different compositions into account, e.g. five to fifty different mixtures so as to represent a representative selection of natural gas compositions, and if temperature and pressure conditions are also taken into account, a very good match can be reached between CVs obtained in theoretical manner and CVs determined using the method of the invention, with the mean difference between the theoretical value and the measured value being practically zero.

The presence of the envelope 22 which is porous to gas but proof against dust serves to limit deposits on the optical components and to avoid interfering absorption due to the light beam passing such non-gaseous substances. Having a parallel light beam also contributes to increasing the volume sampled and to minimizing the risk of any accident on the path through the gas due to residual impurities.

Nevertheless, impurities can end up by being deposited on the optical components, and by a cumulative phenomenon can degrade the dynamic range of measurement.

To mitigate this drawback, it is possible to use a reference wavelength band situated outside the absorption ranges of the gas (e.g. in the range 1.24 μm to 1.25 μm) to normalize transmission in each of the measurement bands.

Under such circumstances, normalized optical transmission $T_i$ in band i is given by:

$$T_i = I_i / I_r$$

where:

$I_i$ is the light intensity measured in band i, and $I_r$ is the light intensity measured in the reference band.

The measured intensity $I_r$ in the reference band also provides information concerning the cleanness of the optical components and provides self-test means for the apparatus.

A first embodiment of the emitter unit 100 and of the receiver unit 200 is described below with reference to FIGS. 4 and 6.

Figure 4:
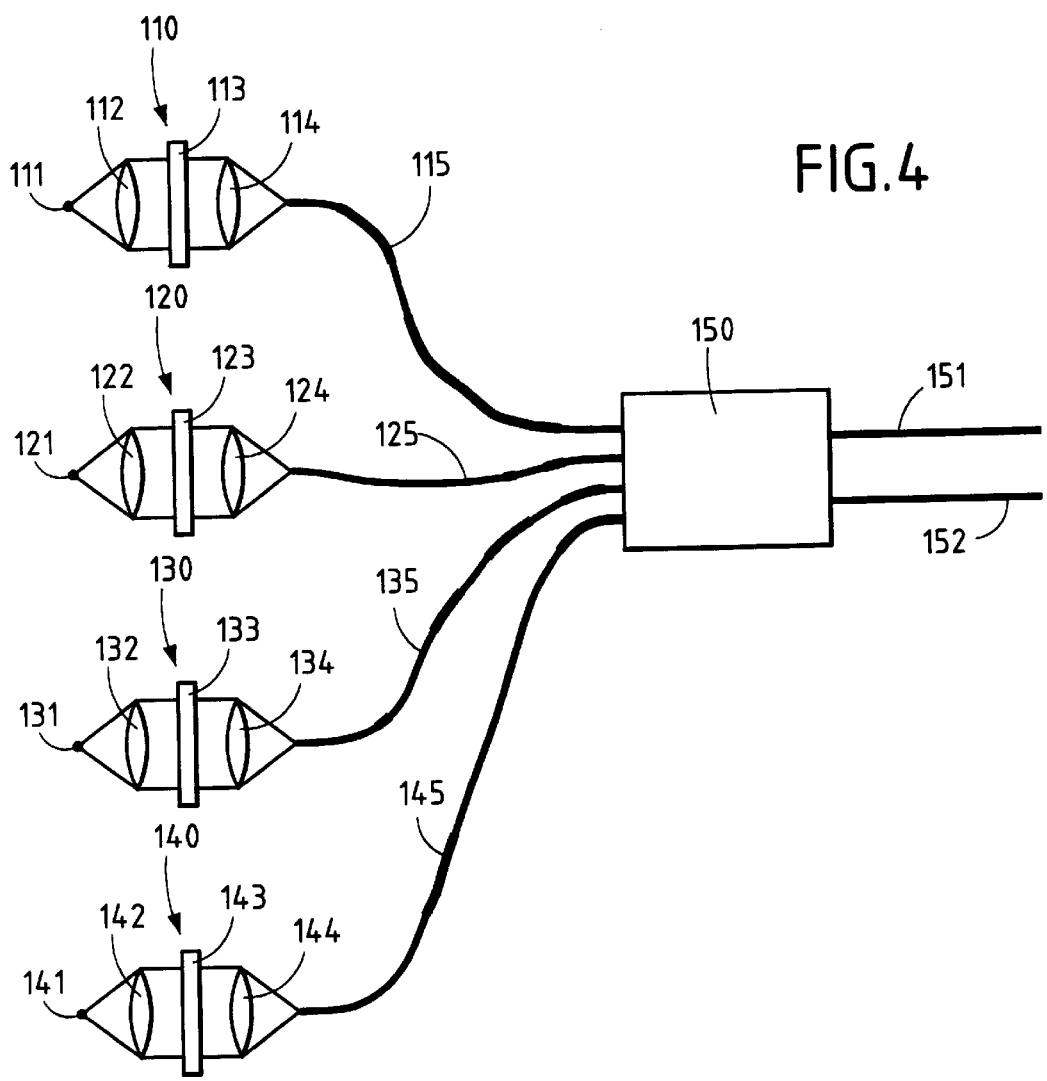
FIG. 4 is a diagram of a first example of an emitter unit usable in the metering apparatus of FIG. 1.

In this embodiment, the light source of the emitter unit 10 comprises, for each measurement band, an emitter module 110, 120, 130, and 140 which is connected by a respective optical fiber 115, 125, 134, and 145 to an optical coupling device 150 (FIG. 4).

Each emitter module 110, 120, 130, 140 comprises a light emitting diode 111, 121, 131, and 141 emitting over a narrow band of wavelengths, having a width of the order of a few tens of nanometers, e.g. 100 nm, a first lens 112, 122, 132, and 142 which spreads out the beam from the corresponding LED 111, 121, 131, and 141 over an interference emitter 113, 123, 133, and 143 and a second lens 114, 124, 134, and 144 which focuses the beam coming from the corresponding interference filter 113, 123, 133, and 143 onto the corresponding optical fiber 115, 125, 135, and 145.

The powers available from sources of this type are about 1.60 µW/nm.

Each measurement band thus has its own source 111, 121, 131, and 141 and its emission is modulated at a corresponding specific frequency f1, f2, f3, f4, e.g. 500 Hz, 1150 Hz, 1600 Hz, and 2200 Hz. The wavelengths 10 of interest for each emission module 110, 120, 130, and 140 are selected by the corresponding interference filter 113, 123, 133, and 143 whose transmission coefficient may be about 50%.

The total light emission supplied by the coupling device 50 is shared over two channels:

a) a measurement channel receiving about 90% of the energy and connected to the measuring head by an optical fiber 151 which corresponds to the fiber 24 in FIGS. 1 to 3, for emitting a light beam to the gas duct; and b) a monitoring channel receiving about 10% of energy which remains available on an optical fiber 152 for checking that the light sources are operating correctly in a self-test mode and when performing maintenance operations. The optical coupling to unit the four channels and then to split them into two channels can be performed within the coupling device 150 e.g. by means of two ATI multimode couplers, one 4-to-1 coupler and one 1-to-2 (10%–90%) coupler connected in series.

The efficiency of such coupling can be of the order of 40%.

Figure 6:
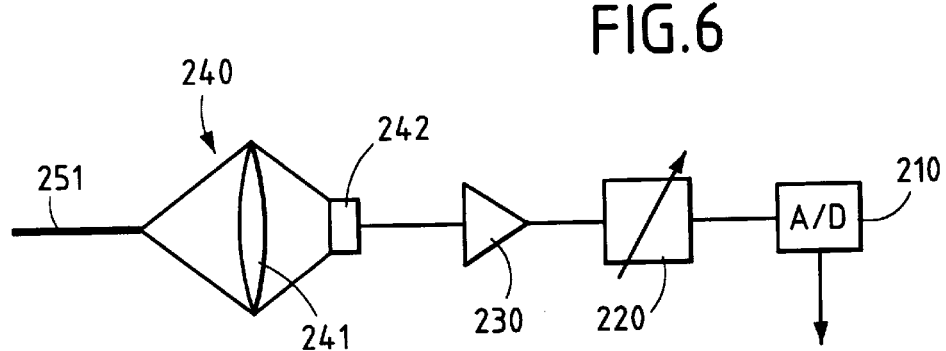
FIG. 6 is a diagram of a first example of a receiver unit usable in the metering apparatus of FIG. 1.

In the receiver unit 200 shown in FIG. 6, at the outlet from optical fiber 251 which corresponds to optical fiber 25 in FIGS. 1 and 3, the signal is applied to a photodetector 240 which has a lens 241 focusing on a detector which can be constituted, for example, by a photodiode 242, typically an InGaAs photodiode having a dark current of about 3 nA and a response of 0.9 A/W at 1300 nm.

The signal incident on the detector 242 is the sum of four components modulated at the four different frequencies f1, f2, f3, and f4, each containing information relating to one measurement channel. The signal from the photodiode 242 is processed in an AC amplifier 230 which transforms the current information delivered by the photodiode 242 into voltage information having a maximum level close to 5 volts, for example.

A demodulator 220 receives the voltage signal from the amplifier 230 and filters the signal at the four modulation frequencies f1, f2, f3, and f4 (i.e. 500 Hz, 1150 Hz, 1600 Hz, and 2200 Hz in the example under consideration). The information relating to each measurement channel is finally digitized in an analog-to-digital converter 210 which delivers a digital signal to the microprocessor 310 of the electronic control module 300. In a variant, filtering need not be performed in analog manner in a demodulator 220. Under such circumstances, the output signal from the amplifier 230 is digitized directly by the analog-to-digital converter 210 and the microprocessor 310 is used to separate the various frequencies by digital filtering and to calculate the amplitudes at these different frequencies.

Figure 5:
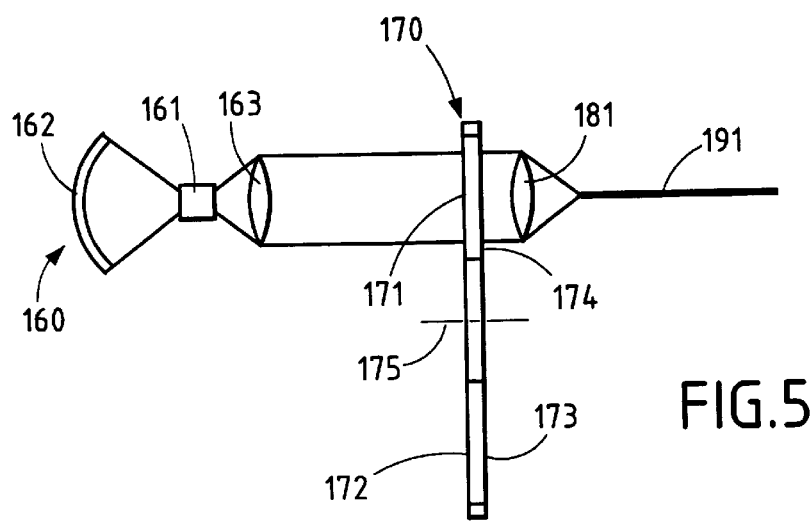
FIG. 5 is a diagram of a second example of an emitter unit usable in the metering apparatus of FIG. 1.
Figure 7:
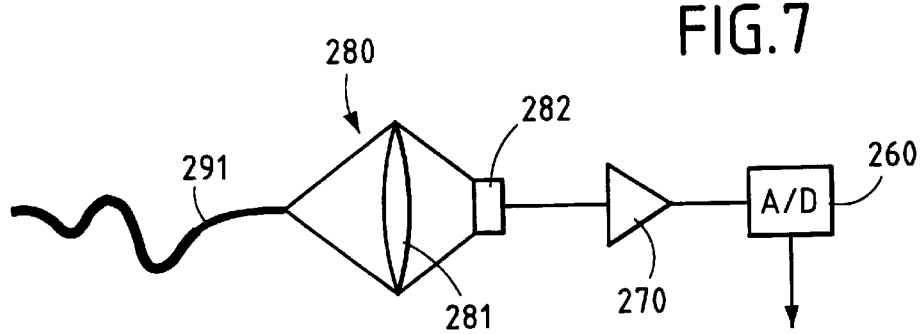
FIG. 7 is a diagram of a second example of a receiver unit usable in the metering apparatus of FIG. 1.

Another embodiment of the emitter unit 100 and the receiver unit 200 is shown in FIGS. 5 and 7.

In the emitter unit 100 shown in FIG. 5, the light source 160 comprises a single broad-spectrum source (black body) such as a tungsten halogen lamp 161 associated with a reflector 162 and a first lens 163 which creates a parallel light beam.

By way of example, for a 20 W lamp 161, the power picked up by the lens, assuming it has a diameter of 2 cm and is placed at 5 cm from the lamp, is about 60 µW/nm in the range 1 µm to 2 µm. It can be assumed that focusing onto the optical fiber 191 (correspond to the optical fiber 24 in FIGS. 1 to 3) by means of a second lens 181 enables 10% of the energy, i.e. 6 µW/nm to be recovered.

A wheel 170 capable of rotating about an axis of rotation 175 carries interference filters 171, 172, 173, and 174 defining the measurement bands, and it is interposed between the lenses 163 and 181, i.e. between the light source 160 and the optical fiber 191 to enable the wavelengths characteristic of the four measurement paths to be selected in succession. This provides time modulation, with measurement rate being tied to the speed of rotation of the wheel 170. By way of example, to operate at 10 Hz, the wheel must rotate at 600 revolutions per minute (rpm). The filtering brings the powers conveyed by the optical fiber 191 to below the safety thresholds.

In the receiver unit 200, shown in FIG. 7, the optical fiber 291 and the photodetector 280 with its lens 281 and its detector 282 constituted by a photodiode may be identical to the corresponding elements 251, 240, 241, and 242 of FIG. 6. When emission is performed by a black body, as in the example of FIG. 5, the incident signal on the photodetector 280 is modulated in time. The current from the photodiode 280 therefore contains information concerning all four measurement channels. This simplifies exploitation of the signal, and the signal from the photodiode 282 can be processed directly in a DC amplifier 270 and can then be digitized in an analog-to-digital converter 260 which delivers a digital signal to the microprocessor 310.

Figure 8:
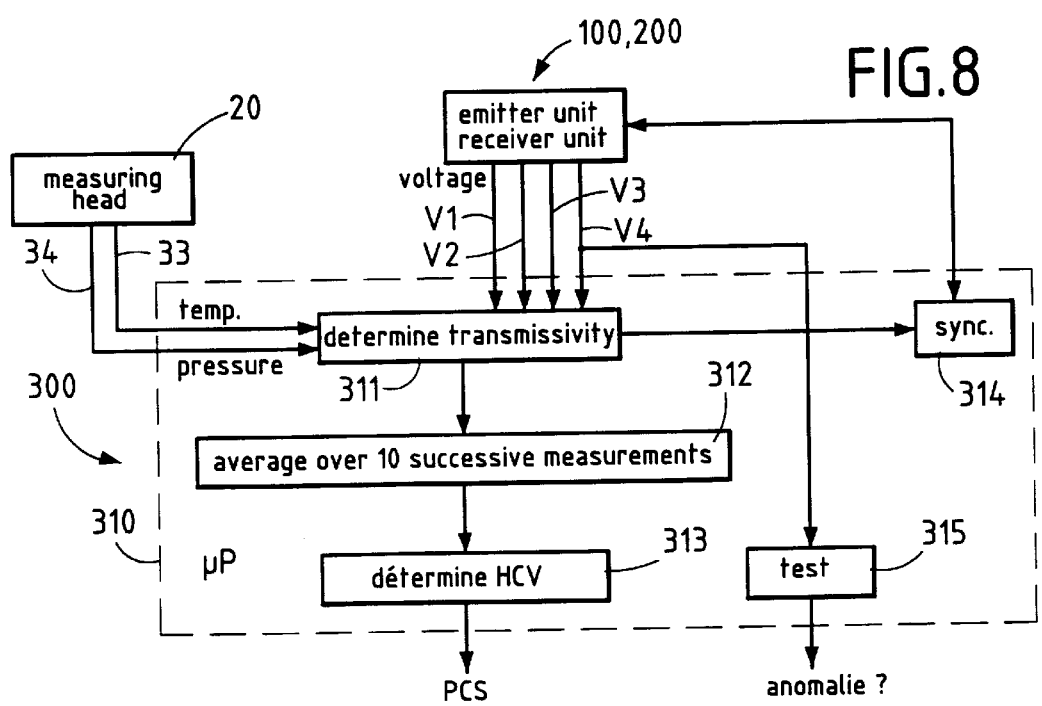
FIG. 8 is a block diagram of an embodiment of an electronic control module usable in the gas metering apparatus of FIG. 1.

The electronic control module 300 shown in FIG. 8 essentially comprises a microprocessor 310 connected to the measuring head 20 to receive over lines 33 and 34 information concerning temperature and pressure, and to the transmitter and receiver units 100, 200 to control synchronization from a synchronization module 314 and to receive digital information concerning voltages $V_1$, $V_2$, $V_3$, and $V_4$ corresponding to the various measurement and reference bands.

The microprocessor 310 thus controls synchronization between the various measurement channels and controls mechanical members, such as the motor driving the filter wheel 170 in FIG. 5, or electrical members such as the circuit for adjusting the demodulation frequency in the demodulator 220 of FIG. 6. The microprocessor acts via a test module 315 to monitor proper operation of the apparatus, e.g. to monitor the cleanness of the optical components by analyzing the signals on the reference channel.

In a functional module 311, the microprocessor processes the information received to determine the mean optical transmission values $T_1$, $T_2$, $T_3$, and $T_4$ on the various measurement channels. In a functional module 313, the microprocessor 310 determines the CV of the gas under consideration, on the basis of the values calculated in the module 311.

To improve the quality of the result, it is possible to perform a series of successive measurements, e.g. ten successive measurements, and to accumulate the results of the ten individual measurements in an intermediate module 312.

After ten measurements have been accumulated, CV is still determined in "real time" since the rate can be 1 Hz.

Without measurement being accumulated, the performance of the metering system is a little less good, however CV can be determined at a rate of about 10 Hz.

It will be observed that the advantage of the present invention consists in using a small number of measurement bands (only three or four) while providing good measurement accuracy.

The method of the invention makes it possible to obtain CV with accuracy that is to within better than 1% over a wide range of gas compositions and of delivery conditions, and it can even be within better than 0.35% for a limited range of gas compositions.

The method of the invention can also be extended to determining additional parameters, other than CV, insofar as a relationship can be established between such a parameter and the infrared absorption of the gas.

Thus, a correlation has been established between the infrared absorption of a gas mixture and the ratio of CV to the square root of density (which parameter is used in calculating the Wobbe index, which is particularly useful for adjusting combustion conditions in burners).

What is claimed is:

1. A method of determining the calorific value of a natural gas optically and in real time by measuring the absorption of a light beam by the components of the gas, in which the gas is illuminated by a light beam of predetermined characteristics, the intensity of the light beam is measured after it has passed through the gas, and the calorific value of the natural gas is calculated from the optical absorption obtained on the basis of the measured intensity of the light beam after it has passed through the gas, wherein the gas is illuminated by means of a light beam defining three measurement bands defining different wavelength ranges, each having a bandwidth of 10 nm to 20 nm and situated in the near infrared, with wavelengths greater than or equal to 1.1 $\mu$m and lower than or equal to 1.8 $\mu$m, the measurement bands define wavelength ranges situated outside the absorption ranges of non-hydrocarbon components, and a reference band is also used defining a range of wavelengths having a bandwidth of 10 nm to 20 nm and situated in the near infrared outside the wavelength ranges of the measurement bands and of the absorption ranges of the gas.

2. A method according to claim 1, wherein the measurement bands are situated in three zones defined by the following wavelength ranges 1.111 $\mu$m to 1.190 $\mu$m, 1.1315 $\mu$m to 1.429 $\mu$m, and 1.613 $\mu$m to 1.818 $\mu$m, in which the hydrocarbons constituting natural gas present significant absorption.

3. A method according to claim 2, wherein the light beams illuminating the gas define three measurement bands defining the following three wavelength ranges: 1.176 $\mu$m to 1.190 $\mu$m; 1.315 $\mu$m to 1.325 $\mu$m; and 1.62 $\mu$m to 1.64 $\mu$m.

4. A method according to claim 1, wherein the reference band defines a wavelength range 1.24 $\mu$m to 1.25 $\mu$m.

5. A method according to claim 1, wherein the pressure and the temperature of the gas are also measured and when determining the calorific value of the natural gas by computation, the measured pressure p and temperature $\theta$ of the gas are taken into account.

6. A method according to claim 1, wherein the calorific value of the natural gas is computed after accumulating a number N of individual measurements of the intensity of the light beam that has passed through the gas, where N is greater than 5.

7. A method according to claim 1, wherein the light beam defines three measurement bands, and wherein the calorific value of the natural gas is deduced from the measured transmission coefficients $T_1$, $T_2$, and $T_3$ of the natural gas in the three measurement bands using the following relationship:

$$CV = \alpha + \beta_1 ln(T_1) + \delta_2 ln(T_2) + \gamma_3 ln(T_3)$$

where $\alpha$, $\beta_1$, $\beta_2$, and $\gamma_3$ represent coefficients determined from calibration tests.

8. A method according to claim 7, wherein the pressure p and the temperature $\theta$ of the gas are also measured, and wherein the light beam defines three measurement bands, and wherein the calorific value of the natural gas is deduced from the measured transmission coefficients $T_1$, $T_2$, and $T_3$ of the natural gas in the three measurement bands using the following relationship:

$$CV = [\alpha(\theta/p) + \alpha_2] + [\beta_{11}(\theta/p) + \beta_{12}]ln(T_1) + [\beta_{21}(\theta/p) + \delta_{22}]ln(T_2) + [\gamma_{31}(\theta/p) + \gamma_{32}]ln(T_3)$$

where $\alpha$, $\alpha_2$, $\beta_{11}$, $\beta_{12}$, $\delta_{21}$, $\delta_{22}$, $\gamma_{31}$, and $\gamma_{32}$ are coefficients determined from calibration tests.

9. A method according to claim 1, wherein the transmission coefficient $T_i$ of the natural gas in a measurement band i is determined by the ratio between the light intensity $I_i$ measured in the measurement band concerned and the light intensity $I_r$ measured in the reference band.

10. Apparatus for determining the calorific value of a natural gas optically and in real time by implementing the method according to claim 1, the apparatus comprising an emitter unit fitted with a light source to cause a light beam to travel in a gas duct, a receiver unit fitted with a photodetector to receive the light beam after it has passed through the gas and to generate signals corresponding to absorption by the gas of the light beam emitted by the source, and an electronic control module for computing the calorific value of the natural gas from the signals emitted by the photodetector, wherein the emitter unit comprises a light source emitting in the near infrared and means for defining three measurement bands constituted by different wavelength ranges each having a bandwidth of 10 nm to 20 nm, wherein the receiver unit comprises a photodetector constituted by a photodiode and an analog-to-digital converter, and wherein the electronic control module has at least one microprocessor.

11. Apparatus according to claim 10, comprising a measuring head comprising a first optical fiber linking it with the emitter unit, a second optical fiber linking it with the receiver unit, a housing into which the first and second optical fibers penetrate and which includes a porthole-forming wall which constitutes a portion of the wall of the gas duct to enable optical collimator components disposed in the housing to emit an incident light beam from the first optical fiber into the inside of the gas duct and to receive from the gas duct a reflected light beam, and a filtering porous envelope disposed inside the gas duct, partially defined by said porthole-forming wall, and containing a retroreflector to receive said incident light beam and to create said reflected light beam.

12. Apparatus according to claim 11, wherein the measuring head is disposed in a gas duct which constitutes a bypass duct in parallel with a main pipe and connected thereto via isolating valves.

13. Apparatus according to claim 10, wherein for each measurement band, the light source comprises an emitter module comprising a light emitting diode emitting a narrow band of wavelengths, having a bandwidth of a few tens of nanometers, the emission of each light emitting diode being modulated at a respective frequency, a first lens which spreads the beam from the corresponding light emitting diode over an interference filter, and a second lens which focuses the beam from the corresponding interference filter onto an optical fiber, and wherein each optical fiber is connected to an optical coupling device.

14. Apparatus according to claim 13, wherein the total emission of light from the optical coupling device is shared mainly over a measurement channel serving to emit a light beam to the gas duct and subsidiarily to a monitoring channel for verifying proper operation of the light source.

15. Apparatus according to claim 13, wherein the receiver unit comprises a lens for focusing on the photodiode of the photodetector, an AC amplifier for transforming the current information delivered by the photodiode into voltage information, and said analog-to-digital converter.

16. Apparatus according to claim 15, wherein the receiver unit further comprises a demodulator which filters the signal at the various modulation frequencies of the emitter modules.

17. Apparatus according to claim 10, wherein the light source comprises a single broadband source such as a tungsten-halogen lamp associated with a reflector and with a first lens, a wheel of interference filters defining the measurement bands and enabling wavelengths characteristic of the various measurement bands to be selected in succession, and a lens for focusing onto an optical fiber.

18. Apparatus according to claim 17, wherein the receiver unit comprises a lens for focusing on the photodiode of the photodetector, a DC amplifier, and said analog-to-digital converter.

19. Apparatus according to claim 10, wherein the electronic control module comprises means for synchronizing the various measurement channels corresponding to the various measurement bands, and means for testing proper operation of the apparatus.

* * * * *